United States Patent [19]
Olesen et al.

[11] Patent Number: 6,063,260
[45] Date of Patent: May 16, 2000

[54] PATCH CLAMP APPARATUS AND TECHNIQUE HAVING HIGH THROUGHPUT AND LOW FLUID VOLUME REQUIREMENTS

[75] Inventors: Søren-Peter Olesen, Klampenborg; Palle Christophersen, Ballerup, both of Denmark

[73] Assignee: NeuroSearch A/S, Ballerup, Germany

[21] Appl. No.: 08/836,094

[22] PCT Filed: Jun. 7, 1995

[86] PCT No.: PCT/EP95/02204

§ 371 Date: Apr. 25, 1997

§ 102(e) Date: Apr. 25, 1997

[87] PCT Pub. No.: WO96/13721

PCT Pub. Date: May 9, 1996

[30] Foreign Application Priority Data

Oct. 28, 1994 [DK] Denmark ................................ 1252/94

[51] Int. Cl.[7] .................................................. G01N 27/33
[52] U.S. Cl. .......................................... 205/793; 204/415
[58] Field of Search .......................... 205/793; 204/415; 73/864.22–864.25, 864.81, 864.83–864.86

[56] References Cited

U.S. PATENT DOCUMENTS

| | | | |
|---|---|---|---|
| 4,128,456 | 12/1978 | Lee et al. | |
| 4,713,974 | 12/1987 | Stone | 73/864.23 |
| 4,889,691 | 12/1989 | Argentieri | 422/102 |
| 5,364,521 | 11/1994 | Zimmermann | 204/604 |
| 5,424,037 | 6/1995 | Zimmermann et al. | 204/601 |

FOREIGN PATENT DOCUMENTS

| | | |
|---|---|---|
| 4305405 C1 | 5/1994 | Germany . |
| WO 85/02201 | 5/1985 | WIPO . |

OTHER PUBLICATIONS

*Patent Abstracts of Europe* (DE 04305405 C1) May 26, 1994 (Assignee: Hering).

*Primary Examiner*—Thomas P. Noland
*Attorney, Agent, or Firm*—The Firm of Gordan W. Hueschen

[57] ABSTRACT

Apparatus for carrying out patch clamp technique utilized in studying the effect of certain materials on ion transfer channels in biological tissue, and more particularly patch clamp apparatus utilizing an autosampler, such as those utilized with HPLC apparatus, to provide high throughput, is disclosed. The invention additionally includes novel microperfusion chamber assemblies capable of utilizing only small amounts of material to be tested and only small amounts of liquid carrier, thereby enabling many tests to be completed in a short period of time. The invention more broadly relates to a novel electrophysiology drug handling and application set up for screening of chemical substances while providing high throughput and requiring only low volume of solutions and samples to be tested. The invention also comprises several novel procedures for utilizing the apparatus of the invention.

20 Claims, 6 Drawing Sheets

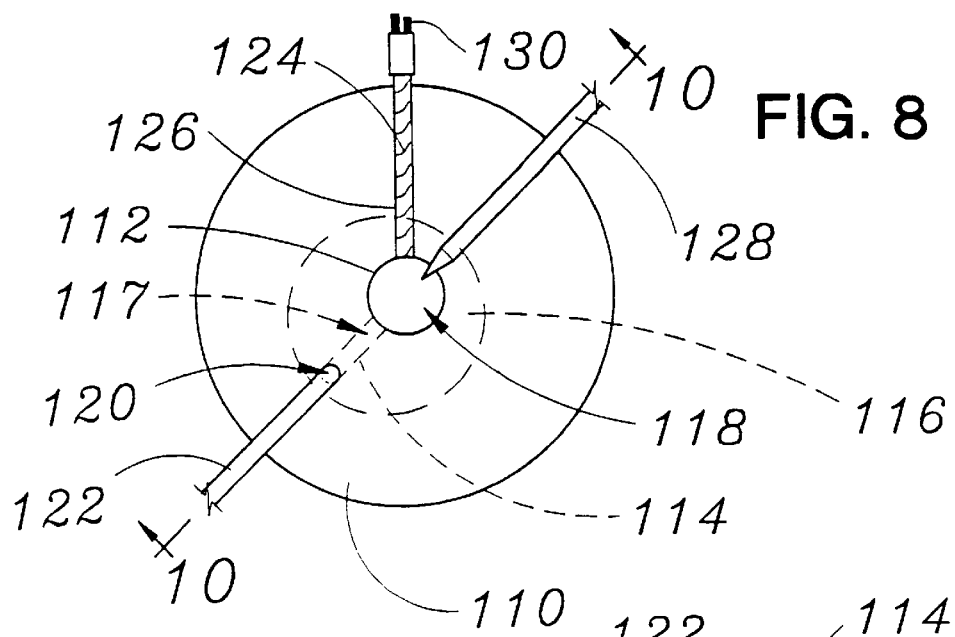
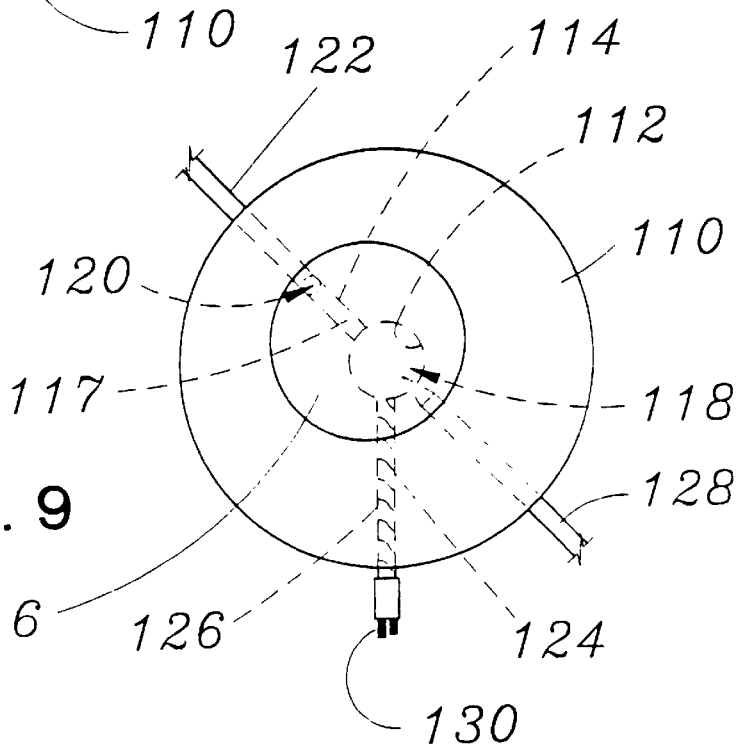
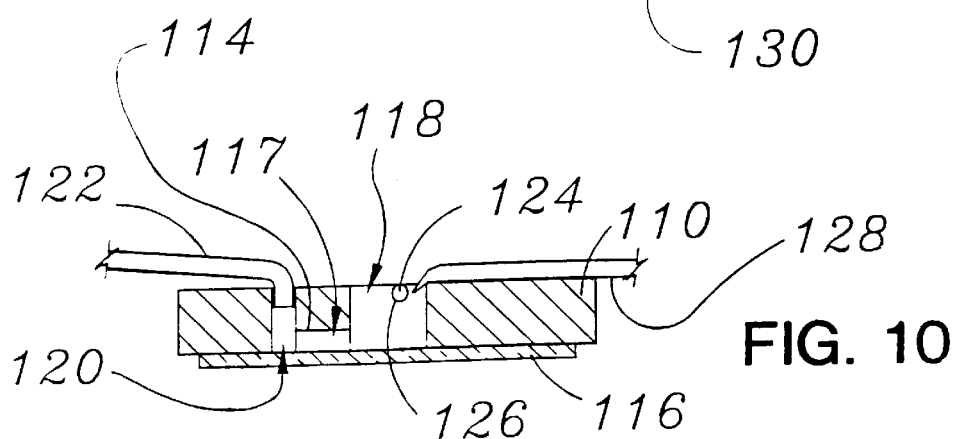

PATCH CLAMP APPARATUS AND TECHNIQUE HAVING HIGH THROUGHPUT AND LOW FLUID VOLUME REQUIREMENTS

BACKGROUND OF THE INVENTION

1. Field of Invention

The present invention relates to apparatus for carrying out patch clamp technique utilized to study ion transfer channels in biological membranes, and more particularly refers to such patch clamp apparatus having high through-put and utilizing only small test samples of compounds, only small amounts of liquid carrier, and capable of carrying out many tests in a short period of time with an individual membrane patch. The invention more broadly refers to a novel electrophysiology drug handling and application set up for screening of chemical substances or compounds, which provides high throughput, and which requires only low volume of solutions and samples to be tested. The invention also comprises several methods for utilizing the apparatus of the invention.

2. Prior Art

The general idea of electrically isolating a patch of membrane using a micropipette and studying the ion channels in that patch under voltage-clamp conditions was outlined by Neher, Sakmann, and Steinback in "The Extracellular Patch Clamp, A Method For Resolving Currents Through Individual Open Channels In Biological Membranes", Pflueger Arch. 375; 219–278, 1978. They found that, by pressing a pipette containing acetylcholine (ACH) against the surface of a muscle cell membrane, they could see discrete jumps in electrical current that were attributable to the opening and closing of ACH-activated ion channels. However, they were limited in their work by the fact that the resistance of the seal between the glass of the pipette and the membrane (10–50 MΩ) was very small relative to the resistance of the channel (~10 GΩ). The electrical noise resulting from such a seal is inversely related to the resistance and was large enough to obscure the currents through ion channels, the conductances of which are smaller than that of the ACH channel. It also prohibited the clamping of the voltage in the pipette to values different from that of the bath due to the large currents through the seal that would result.

It was then discovered that by fire polishing the glass pipettes and applying gentle suction to the interior of the pipette when it made contact with the surface of the cell, seals of very high resistance (1–100 GΩ) could be obtained, which reduced the noise by an order of magnitude to levels at which most channels of biological interest can be studied and greatly extended the voltage range over which these studies could be made. This improved seal has been termed a "giga-seal", and the pipette has been termed a "patch pipette". For their work in developing the patch clamp technique, Neher and Sakmann were awarded the 1991 Nobel Prize in Physiology and Medicine.

Ion channels are transmembrane proteins, which catalyze transport of inorganic ions across cell membranes. The ion channels participate in processes as diverse as generating and timing of action potentials, synaptic transmission, secretion of hormones, contraction of muscles, etc. Many drugs exert their specific effects via modulation of ion channels. Examples are antiepileptic compounds like phenytoin and lamotrigine, which block voltage dependent $Na^+$-channels in the brain, antihypertensive drugs like nifedipine and diltiazem, which block voltage dependent $Ca^{2+}$-channels in smooth muscle cells, and stimulators of insulin release like glibenclamide and tolbutamide, which block an ATP-regulated $K^+$-channel in the pancreas. In addition to chemically induced modulation of ion-channel activity, the patch clamp technique has enabled scientists to perform voltage dependent channel manipulations. These techniques include adjusting the polarity of the electrode in the patch pipette and altering the saline composition to moderate the free ion levels in the bath solution.

The patch clamp technique represents a major development in biology and medicine, since this technique allows measurement of ion flow through single ion channel proteins, and also allows the study of the single ion channel responses to drugs. In brief, in standard patch clamp technique, a thin (<1 $\mu$m in diameter) glass pipette is used. The tip of this patch pipette is pressed against the surface of the cell membrane. The pipette tip seals tightly to the cell and isolates a few ion channel proteins in a tiny patch of membrane. The activity of these channels can be measured electrically (single channel recording) or, alternatively, the patch clamp can be ruptured allowing measurements of the channel activity of the entire cell membrane (whole cell recording).

During both single channel recording and whole-cell recording, the activity of individual channel subtypes can be further resolved by imposing a "voltage clamp" across the membrane. Through the use of a feedback loop, the "voltage clamp" imposes a voltage gradient across the membrane, limiting overall channel activity and allowing resolution of discrete channel subtypes.

The time resolution and voltage control in such experiments are impressive, often in the msec or even $\mu$sec-range. However, a major obstacle of the patch clamp technique as a general method in pharmacological screening has been the limited number of compounds that could be tested per day (typically no more than 1 or 2). Also, the very slow rate of solution change that can be accomplished around cells and patches may constitute a major obstacle.

A major limitation determining the throughput of the patch clamp technique is the nature of the feeding system, which leads the dissolved compound to perfused cells and patches. In usual patch clamp setups, cells are placed in large experimental chambers (0.2–2 ml), which are continuously perfused with a physiological salt solution. Compounds are then applied by changing the inlet to a valve connected to a small number of feeding bottles. However, a number of problems exist in the technique of the prior art. First, the number of different compounds is limited by the number of bottles that may be connected to the application system at one time. This number is usually less than 6. Second, the required volumes of the supporting liquid and the sample to be tested are critically high. Third, the time needed to change the solute composition around cells and patches is long for usual patch clamp experiments. Fourth, the introduction and application of compounds to be tested usually involves a significant degree of manual manipulation and interruption, thus jeopardizing the integrity of the cell/pipette connection.

The development of sophisticated systems for local application of compounds to activate neurotransmitter regulated channels, like the U-tube and other systems, reduces the effective application times to 10–100 msec, which is often acceptable. However, the volume of bath solution needed to be exchanged by these fast application systems is quite large and results in a limited capacity for screening multiple compounds per day. This presently limits the use of these procedures in medical industry. A major reason is the inflexibility and low capacity of the feeding systems which fill the U-tube. These are virtually identical to the systems used in conventional patch clamp experiments and therefore are still burdened with the inconveniences of these systems.

OBJECTS OF THE INVENTION

According to the present invention, it has surprisingly been found that it is possible to combine the patch clamp technique with the use of an autosampler, a combination which was unobvious at the outset to a person skilled in the art, especially due to the fact that the technique is sensitive to disturbances, such as vibrations and electrical noise arising from the autosampler, so that it would at best have been considered an impossible or inoperative combination.

It is an object of the present invention to provide and adapt apparatus for automatic drug handling and application, and to utilize the apparatus in an electrophysiological system for screening of chemical substances or compounds to measure their effect on ion channel transfer, the novel system providing high throughput and low fluid volume requirements.

It is a further object of the present invention to reduce the needed amount of any chemical compound for testing as well as to increase the rate of screening, thereby providing the first electrophysiology test system suitable for commercial pharmaceutical company screening.

It is still further an object to provide novel microperfusion chamber structures having microperfusion chambers of extremely low volume.

It is still an additional object of the invention to provide novel methods for carrying out patch clamp technique utilizing the apparatus of the present invention. The foregoing and other objects, advantages, and characterizing features of the invention will become apparent from the following description of certain illustrative embodiments thereof considered together with the accompanying drawings, wherein like reference numerals signify like elements throughout the various figures.

SUMMARY OF THE INVENTION

What we believe to be our invention, then, inter alia, comprises the following, singly or in combination:

An apparatus for determining the effect of test samples of compounds on ion-transfer channels of a membrane, comprising:

an autosampler having a plurality of containers adapted to contain test samples in solution, and having means for automatically withdrawing said test samples from each of said containers and discharging them into a receptacle, a container adapted to contain a supporting liquid, a perfusion chamber adapted to receive a test sample in solution, a supporting liquid, and said membrane, said perfusion chamber comprising a reference electrode adapted to contact electrically a solution contained in said chamber, means for transporting said test samples in solution from the receptacle of said autosampler and said supporting liquid from its container into said perfusion chamber, and means for removing said test sample and said supporting liquid from said perfusion chamber, a patch pipette having an electrode therein, movably positioned over said perfusion chamber and adapted to provide a high electrical resistance seal with the surface of a patch of said membrane positioned within said chamber, and means electrically connected to said patch pipette electrode and said reference electrode for measuring the current passing through said electrodes before and after the introduction of said test sample into said perfusion chamber;

such apparatus wherein the means for transporting test samples and supporting liquid to said perfusion chamber includes a U-tube mounted over said perfusion chamber and having an aperture therein for releasing a test sample and its supporting liquid into said perfusion chamber; and apparatus for determining the effect of test samples of compounds on ion-transfer channels of a membrane, comprising:

an autosampler having a plurality of containers adapted to contain test samples in solution, and having means for automatically withdrawing said test samples from each of said containers and discharging them into a receptacle, a container adapted to contain a supporting liquid, a microperfusion chamber adapted to receive a test sample in solution, a supporting liquid, and said membrane, the volume of said microperfusion chamber being about 5 microliters to about 50 microliters, said microperfusion chamber comprising a reference electrode adapted to contact electrically a solution contained iii said chamber, means for transporting a test sample in solution from the receptacle of said autosampler and said supporting liquid from its container into said microperfusion chamber and means for removing said test sample and said supporting liquid from said microperfusion chamber, a patch pipette having an electrode therein, movably positioned over said microperfusion chamber and adapted to provide a high electrical resistance seal with the surface of a patch of said membrane positioned within said chamber, and means electrically connected to said patch pipette electrode and said reference electrode for measuring the current passing through said electrodes before and after the introduction of a test sample into said microperfusion chamber;

such apparatus wherein the volume of said microperfusion chamber is in the range of about 10 microliters to about 15 microliters; such apparatus wherein the volume of said microperfusion chamber is in the range of about 10 microliters to about 12 microliters; such apparatus having means for aspirating waste liquid from said microperfusion chamber; such apparatus wherein said means of said autosampler for automatically withdrawing said test samples from said containers and discharging them into a receptacle comprises a syringe pump and a needle connected thereto; and such apparatus wherein a tubular coil is positioned in series with said means for transporting said test sample for quantitatively determining the volume of the sample introduced into said microperfusion chamber.

Also, a microperfusion chamber assembly comprising: a base, an aperture in said base, and transparent means over the bottom of said base, said aperture and said transparent means cooperating to define the side walls and the bottom of a microperfusion chamber, a reference electrode arranged to contact a liquid in said chamber, means for introducing a liquid into said chamber, means for aspirating liquid from said chamber, and means for electrically connecting said reference electrode to an electrical measuring device;

such a microperfusion chamber assembly wherein said transparent means forming the bottom of said chamber is a transparent coverslip; such a microperfusion chamber assembly wherein said base comprises silver having a coating of a silver halide deposited over at least the surface of the aperture defining the side walls of said microperfusion chamber, thereby providing a reference electrode in said base adapted to make electrical contact with a liquid contained in said chamber; such a microperfusion chamber assembly wherein said base comprises silver having a coating of silver chloride deposited over at least the surface of the aperture defining the side walls of said microperfusion chamber; such a microperfusion chamber assembly wherein said base comprises silver having a coating of silver chloride deposited over its entire surface including the side walls of said chamber; such a microperfusion chamber assembly wherein said microperfusion chamber is cylindrical, frustoconical, or ellipsoid; such a microperfusion chamber assembly wherein the volume of said microperfusion chamber is about 5 microliters to about 50 microliters; such a microperfusion chamber assembly wherein the volume of said microperfusion chamber is about 10 microliters to about 15 microliters; such a microperfusion chamber assembly wherein the volume of said microperfusion chamber is about 10 microliters to about 12 microliters; and a microperfusion chamber assembly comprising a base formed of a non-electrically conductive material, an aperture provided in said base, and transparent cover means at the bottom of said base, said aperture and said transparent cover means cooperating to define the side walls and bottom of a microperfusion chamber, a reference electrode mounted in said base extending through a side wall of said microperfusion chamber and arranged electrically to contact a liquid contained in said chamber, means for introducing a liquid into said chamber, means for aspirating liquid from said chamber, and means for electrically connecting said reference electrode to an electrical measuring device;

such a microperfusion chamber assembly wherein said base comprises a plastic material; such a microperfusion chamber assembly wherein said plastic material is polymethyl methacrylate, polystyrene, polyvinyl chloride, or polycarbonate; such a microperfusion chamber assembly wherein said electrode comprises a silver wire surrounded by a mixture of particulate silver and a silver halide; such a microperfusion chamber assembly wherein said electrode comprises a silver wire surrounded by a mixture of particulate silver and silver chloride; such a microperfusion chamber assembly wherein said particulate silver and silver chloride are affixed to said silver wire; such a microperfusion chamber assembly wherein said means for introducing a liquid into said microperfusion chamber is a groove provided in said base cooperating with said transparent cover means to define a channel, the proximal end of said channel communicating with said microperfusion chamber, and an aperture provided at the top of said base communicating with the distal end of said channel and adapted to have an inflow duct connected thereto for introducing a liquid into said microperfusion chamber;

such a microperfusion chamber assembly wherein the volume of said microperfusion chamber is about 5 microliters to about 50 microliters; such a microperfusion chamber assembly wherein the volume of said microperfusion chamber is about 10 microliters to about 15 microliters; and such a microperfusion chamber assembly wherein the volume of said microperfusion chamber is about 10 microliters to about 12 microliters.

Also, a method for determining the effect of test samples of compounds on ion-transfer channels of a membrane contained in a perfusion chamber, wherein a patch pipette having an electrode therein has its tip engaged in a giga-ohm seal with the surface of said membrane, and wherein a reference electrode is provided in said chamber adapted to contact a solution contained in said chamber, comprising:

continuously or periodically introducing a supporting liquid containing ions, the transfer characteristics of which are to be determined as a baseline reference, into said chamber, periodically loading one of said test samples dissolved in the same supporting liquid into said chamber utilizing an autosampler having a plurality of containers holding test samples in solution, and measuring the electrical current flowing in an electrical measuring means circuit connected between said pipette electrode and said reference electrode both before and after introduction of said test sample into said perfusion chamber, and repeating the procedure; such a method wherein said supporting liquid is continuously introduced into said perfusion chamber and the excess aspirated, and wherein said autosampler is programmed periodically to introduce a test sample into the flowing stream of said supporting liquid to flow therewith into said perfusion chamber; such a method wherein said perfusion chamber is a microperfusion chamber having a volume of 5 microliters to about 50 microliters; such a method wherein the volume of said microperfusion chamber is about 10 microliters to about 15 microliters; such a method wherein the volume of said microperfusion chamber is about 10 microliters to about 12 microliters; such a method wherein said supporting liquid is periodically introduced into said perfusion chamber and the excess aspirated, and wherein said autosampler is programmed periodically to cause a test sample to flow into said perfusion chamber; such a method wherein some of said containers in said autosampler contain said supporting liquid and wherein said autosampler is programmed periodically to introduce said supporting liquid and said test sample sequentially into said perfusion chamber; such a method wherein only small volumes of both test samples and supporting liquid are employed, wherein said perfusion chamber is a microperfusion chamber having a volume of about 5 to about 50 microliters, wherein some of the containers in said autosampler contain said supporting liquid, and wherein said autosampler first aspirates a volume of supporting liquid from one of said containers and causes the supporting liquid to enter said microperfusion chamber, and wherein said autosampler subsequently aspirates a test sample from one of said containers and causes the test sample to enter said microperfusion chamber and to replace said supporting liquid in said chamber, and wherein an electrical measurement is made both when said supporting liquid and when said test sample are present in said microperfusion chamber; such a method wherein the volume of said microperfusion chamber is about 10 microliters to about 15 microliters; such a method wherein the volume of said microperfusion chamber is about 10 microliters to about 12 microliters; such a method wherein an external electrical current is imposed on said electrodes to bring the reference current to the desired value; and such a method wherein an external electrical current is imposed on said electrodes to bring the reference current to the desired value.

DESCRIPTION OF THE DRAWINGS

FIG. 8 is a top plan view of the microperfusion chamber plate of the assembly shown in FIG. 7.

FIG. 9 is a bottom plan view of the microperfusion chamber plate of the assembly shown in FIG. 7.

FIG. 10 is a cross-sectional view taken at the line 10—10 of FIG. 8.

DESCRIPTION OF THE PREFERRED EMBODIMENTS

The present invention provides apparatus for carrying out patch clamp techniques utilizing an autosampler such as that utilized with HPLC apparatus to provide a very rapid means for carrying out a large number of experiments in a short period of time. The invention also permits carrying out patch clamp experiments utilizing only small amounts of test sample and small amounts of supporting liquid. The present invention also provides several novel structures for microperfusion chambers capable of supporting patch clamp studies while utilizing only very small amounts of the test samples and very small amounts of supporting liquid. The present invention also provides several different procedures for carrying out patch clamp experiments utilizing the novel apparatus.

Figure 1:
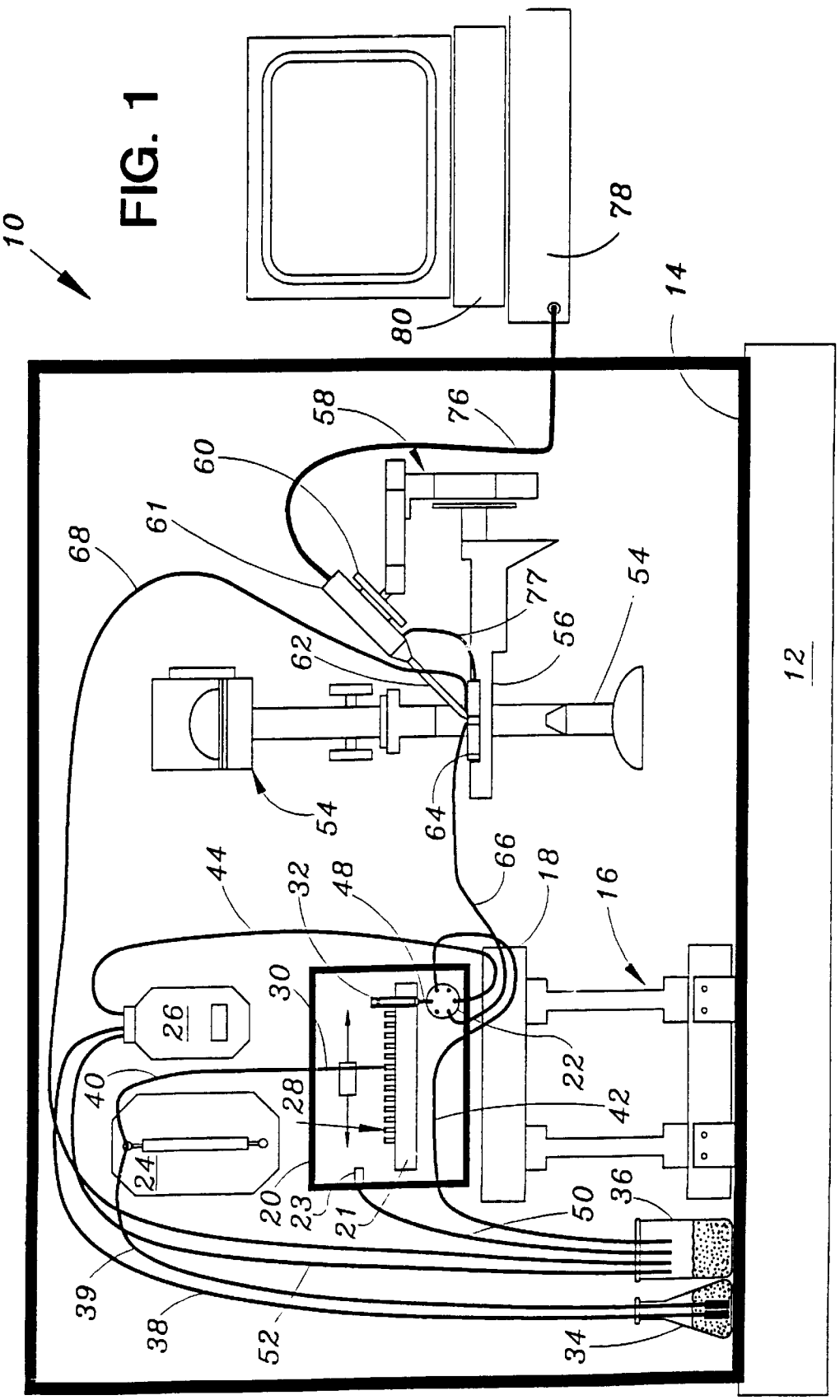
FIG. 1 is a schematic view of a general assembly of components utilized in combination in practicing the several embodiments of the present invention.

Referring to FIG. 1, a general assembly of components for practicing the present invention is shown. The arrangement shown is particularly designed for use in practicing the embodiment of the invention termed the "continuous flow technique". However, with a few modifications the assembly may be utilized in practicing other embodiments of the invention to be described. The assembly of components 10 comprises an air table 12 supporting a Faraday cage 14. Mounted within the Faraday cage 14 is a bridge 16 supporting a table top 18. An autosampler 20 (Gilson Model 231 SL), generally used with an HPLC (High Performance Liquid Chromatograph) system, and equipped with a multiple connection valve 22, is mounted on the table top 18, together with a syringe pump 24, and a peristaltic pump 26 (Gilson Model Minipuls 3). Test compounds in solution are contained in sample containers 28, arranged in an autosampler tray 21. A needle 30, a component of the autosampler 20, is mounted to be movable both laterally and vertically among the containers 28. A rinsing station 23 is provided to collect solution used in rinsing the needle 30. An injection port 32 communicates with the multiple connection valve 22. The syringe pump 24 is connected to the needle 30 by a duct 40 and, when in operation, causes the needle 30 to draw up a measured volume of liquid from a preselected sample container 28 at a specific position in the autosampler tray 21. When the needle 30 has drawn a sample in solution to be tested, it moves to the injection port 32 and injects the sample therein.

A supporting fluid container 34, adapted to contain a fluid such as a physiological saline solution, is mounted within the Faraday cage 14. A waste collection container 36 is also mounted within the Faraday cage 14. A plurality of ducts connect the various components of the assembly together for the purpose of transporting fluids among them. For example, a duct 38 connects the supporting fluid container 34 to the peristaltic pump 26; a duct 39 connects the supporting fluid container 34 to the syringe pump 24; a duct 40 connects the needle 30 to the syringe pump 24; a duct 42 connects the valve 22 to the waste collection container 36; a duct 44 connects the peristaltic pump 26 to the multiple connection valve 22; a duct 48 connects the injection port 32 to the microperfusion chamber valve 22; a duct 50 connects the rinsing station 23 to the waste collection container 36; and a duct 52 connects the peristaltic pump 26 to the waste container 36.

Mounted on a separate table is an inverted microscope 54 (Nomarski optics, Olympus model EPC-9) having a stage 56. The microscope itself is attached to the movable part of the table. At least one electronic micromanipulator 58 (Eppendorf) is also mounted on the microscope stage 56, and supports a patch pipette electrode holder 60 having mounted thereon a preamplifier (headstage) 61 and a conventional patch pipette 62 and which may optionally hold other electrodes for completing voltage and current clamp loops. A microperfusion chamber plate 64 is mounted on the microscope stage 56 and includes a microperfusion chamber 72. A supply duct 66 connects an outlet from the multiple connection valve 22 to an inlet of the microperfusion chamber plate 64, and a waste duct 68 connects the waste port of the microperfusion chamber plate 64 to a vacuum source for removal of waste. The distance from the valve 22 outlet to the microperfusion chamber 72 is 10 cm to minimize the dead-space. The electrode within the patch pipette 63 and the reference electrode are both connected to the preamplifier (headstage) 61. Electrical wire 76 connects the preamplifier (headstage) 61 to the voltage amplifier 78. Electrical wire 77 connects a reference electrode within the microperfusion chamber 72 with the preamplifier (headstage) 61. Any further voltage or current clamp electrode wires are connected to the amplifier designed to establish the desired current or voltage gradient by the preamplifier (headstage) 61. The voltage amplifier 78 is in turn electrically connected to a computer 80 used to measure the electrical impulses indicating the passage of ions through ion channel proteins of the membrane or cell being tested. The electronic micromanipulator 58 carrying the patch pipette holder 60 is mounted on the right side of the microscope stage 56.

To obtain well-defined applications to cells or membranes and to utilize only small volumes of test samples and supporting liquids, the valve 22 outlet should be as close as possible to the microperfusion chamber, or to the U-tube when this component is utilized. Therefore the autosampler itself is placed within the Faraday cage, as shown in FIG. 1, close to the head-stage (preamplifier) 61 of the patch clamp amplifier 78 and the patch pipette 62, which is in contact with the membrane being tested. This raises two potentially serious problems:

1) Electrical noise. The introduction into a Faraday cage of any device which has to be powered by an alternating voltage will result in a source of 50 Hz or 60 Hz electromagnetic radiation. This may easily be picked up by the electrode in the patch pipette 62 (working as an antenna), thus disturbing the current signal. However, careful grounding of all metallic parts of the entire setup to a common high-quality ground will essentially solve this problem. Special care must be taken to ground and shield critical parts of the autosampler 20 to avoid excess electrical noise. When using other autosamplers, which possibly may be more difficult to ground effectively than the Gilson model utilized in the set-up shown in FIG. 1, it may become necessary to shield the autosampler in a separate Faraday cage.

2) Vibrations. Vibrations are created by the autosampler 20 when the needle 30 moves between sample containers 28. This has two implications: 1) Vibrations transferred to the pipette 62 will inevitably destroy the giga-seal (giga-ohm seal) in cell-attached as well as in whole cell recording modes. 2) Even weak mechanical vibrations may be transduced into low-frequency electrical noise appearing in the current signal. However, with the bridge set-up illustrated in FIG. 1, both problems are avoided.

The procedure is carried out by placing a membrane having ion channels into the microperfusion chamber 72. The patch clamp procedure may be more conveniently carried out by inserting a small coverslip 74 (2.8 mm), on which the cultured cells may be positioned within the microperfusion chamber 72. The patch electrode pipette 62 is then lowered into the microperfusion chamber 72 until it comes into contact with the membrane supported on the small coverslip 74. Suction is applied to the patch pipette 62 until a giga-seal (giga-ohms) is created between the end of the patch pipette 62 and the biological membrane. Testing is then carried out. An electrical signal is detected by an electrode in the patch pipette 62 attached to the preamplifier (headstage) 61, and then is transmitted by electrical wire 76 to the voltage amplifier 78 and the computer 80, shown in FIG. 1. A reference electrode (not shown) in contact with the solutions in the chamber is connected to the ground terminal of the preamplifier (headstage) 61.

Various supporting solutions can be adapted for use in the patch clamp procedure depending on the protocol appropriate for the compounds to be tested. A standard solution used for recording of calcium-activated potassium channels comprises (in mM) 140 KCl, 1 $CaCl_2$, 1 $MgCl_2$, 1.3 EGTA, 10 HEPES. This composition results in a free calcium concentration in solution of 0.3 $\mu$M. Calcium ion-induced K-channel activation can be achieved by changing the EGTA concentration to 1.07 mM, resulting in a free calcium concentration in solution of 1.0 $\mu$M. Test compounds are dissolved in the supporting solution depending on the protocol of the assay chosen. All test compound solutions and physiological saline solutions are filtered before use in the apparatus.

In the continuous flow adaptation of the technique and referring to FIG. 1, a continuous flow of the supporting liquid is established by the peristaltic pump 26. Periodically, the autosampler 20 aspirates a specified volume of test compound from a chosen sample vial 28 and loads it into a tubular loop 70 (total loop filling) via injection port 32. The sample volume, loop volume, flow rate, etc. are optional. After loading, the outlet of the multiple connector valve 22 changes and the loop content is conducted by the duct 66 from the valve to the microperfusion plate into the microperfusion chamber 72 from which excess fluid is removed by aspiration. The duration of test compound application is determined by the loop size and the flow rate. The wash out time of the compound is optionally determined by the period between injections. The autosampler changes chamber solutions automatically according to a predefined program. The number of compounds tested between washout periods varies according to the chosen protocol.

The specific advantages of the present continuous flow system compared to more conventional continuous flow systems, are:

1) Automatic change of test solutes.
2) Extensive and flexible coordination between autosampler and patch clamp amplifier.
3) Flexibility of compound application, change of programs during experiments, etc.
4) Automatic dissolution of compounds just prior to the testing of the compound (important for unstable materials).
5) Automatic rinsing of needle and injection port to avoid carry over between individual applications.

Figure 2:
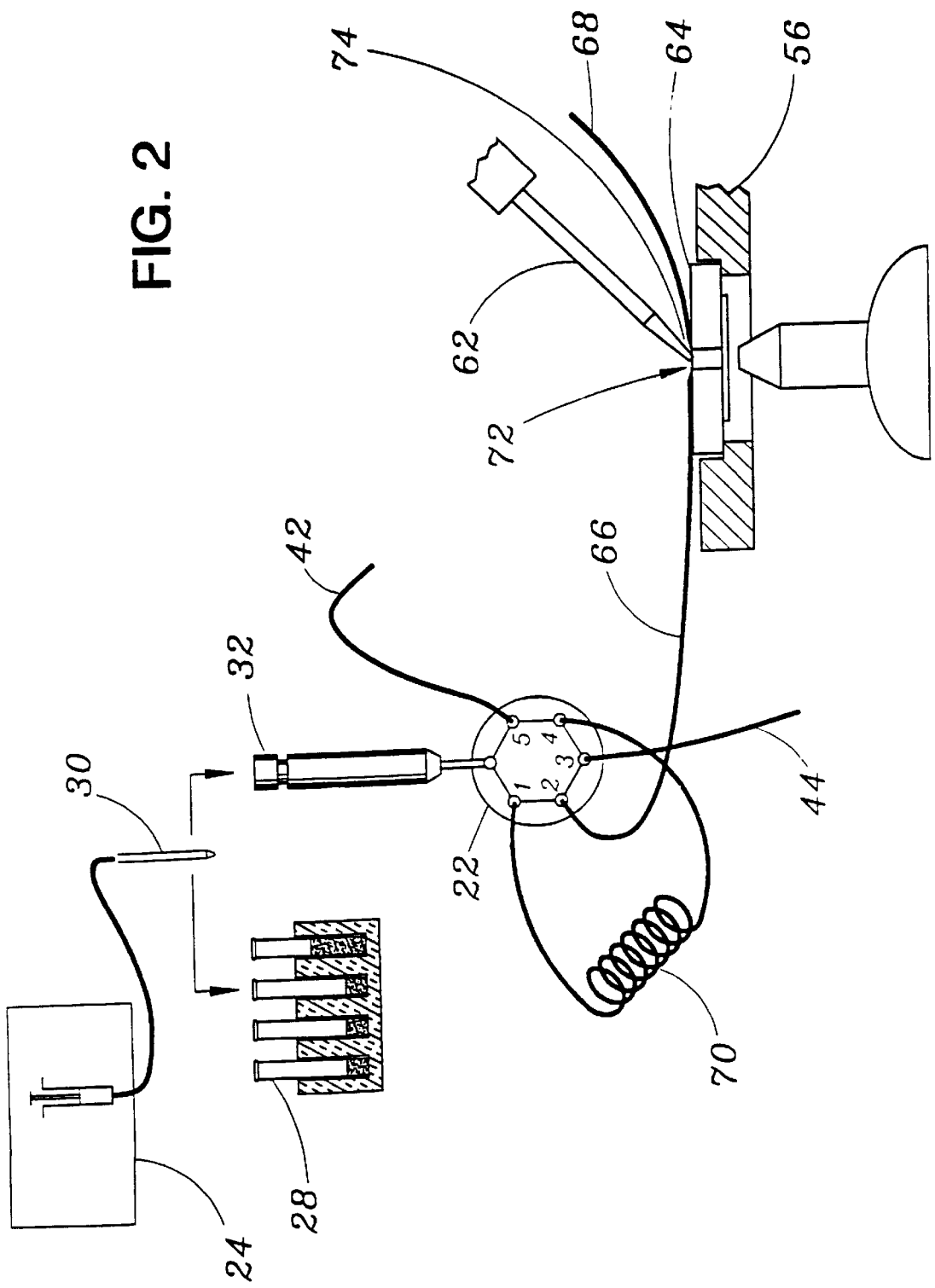
FIG. 2 is a schematic view of a portion of the apparatus as it is utilized in practicing the continuous flow technique of the present invention.

Referring to FIG. 2, the details of the continuous flow technique utilizing the apparatus shown in FIG. 1 are shown in schematic diagram. In operation, a physiological saline solution, or other supporting liquid is pumped at a steady rate by the peristaltic pump 26 through the valve 22 and on to the microperfusion chamber 72. Fluid is also continuously aspirated by vacuum from the microperfusion chamber 72 via the duct 68. The procedure continues as follows:

a) A small volume of air is aspirated into the needle 30 by the syringe pump 24.
b) The needle 30 is moved to a sample vial 28 and aspirates a specified volume of sample.
c) The needle 30 is moved to the injection port 32 and loads the tubular loop 70 with the sample (usually 3 times loop volume; excess volume is rejected through outlet 5 of the multiple connector valve 22).

d) The multiple connector valve 22 changes to the injection mode and the tubular loop 70 content is injected into the duct 66 from the valve 22 to the microperfusion chamber 72.

e) The multiple connector valve 22 changes to the continuous flow mode and the saline solution continues to flow after the sample aliquot being tested.

f) Before the next application is initiated, the needle 30 is rinsed (perfusion on both sides with reservoir solution) in the rinsing station 23. Reservoir solution is drawn up from the supporting fluid container 34 through the duct from the supporting fluid container 39 and discarded through the needle 30 at the rinsing station 23. The injection port 32 is rinsed by loading reservoir saline through the valve 22 with waste solution discarded through outlet 5.

Figure 3:
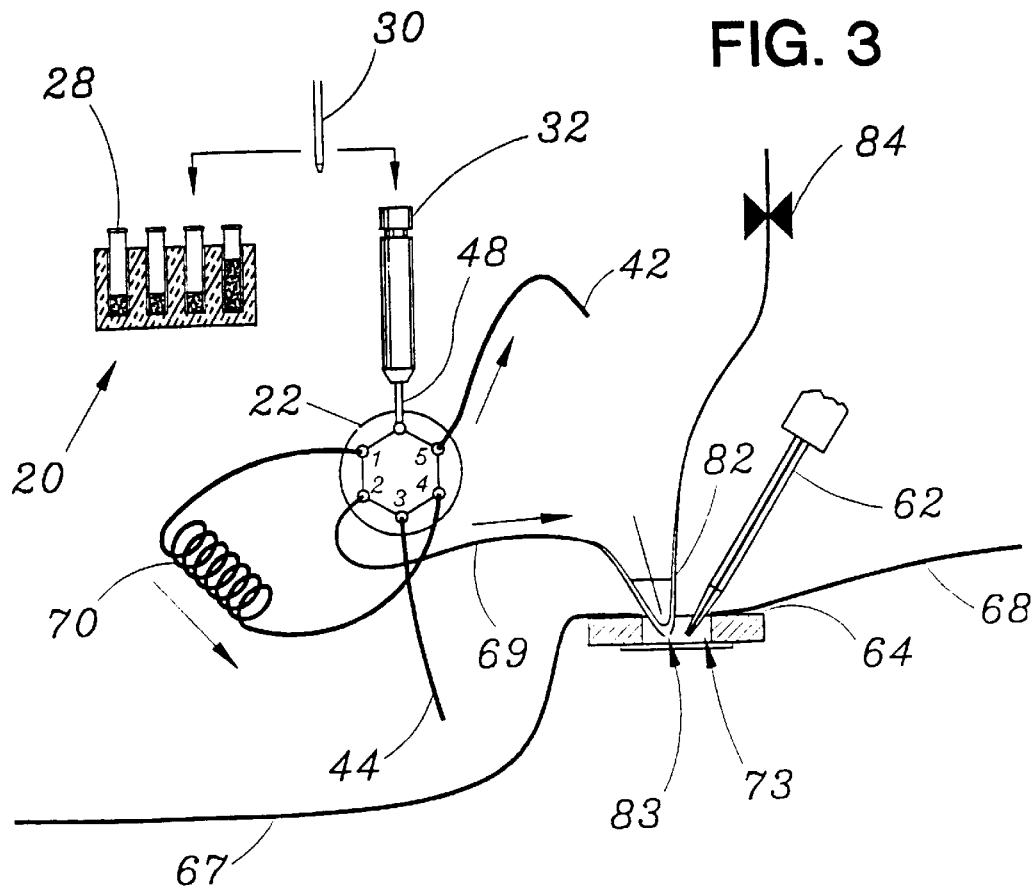
FIG. 3 is a schematic view of a portion of the apparatus as it is modified and utilized in practicing the U-Tube technique of the present invention.

Referring to FIG. 3, a modified embodiment of the invention is shown which is utilized to carry out the U-tube technique. The components utilized in carrying out the method of this embodiment are substantially the same as those shown in FIG. 1, with the exception that the test sample is discharged into the perfusion chamber 73, through an aperture 83 provided in the bottom of a U-tube 82.

Conventional fast application systems like the U-tube system are easily served by the apparatus of the present invention, including the autosampler. Cells are placed in a somewhat larger perfusion chamber than that used in the continuous flow technique described above. This facilitates positioning of the U-tube. The autosampler operates in the U-tube technique in much the same manner as it operates in the continuous flow technique described above. The membrane is continuously perfused by normal saline solution pumped at a steady rate by the peristaltic pump 26 through a duct 67 from the peristaltic pump 26 to the perfusion chamber 73 (this duct does not pass through the multiple connection valve 22). Fluid is also continuously aspirated from the perfusion chamber 73 via duct 68 and the peristaltic pump. The peristaltic pump also continuously pumps normal saline through the U-tube 82. The fluid is pumped through the multiple connection valve 22 and on to the U-tube through duct 69. Because of the reduced pressure within the U-tube resulting from the fluid flow, a small amount of fluid from the perfusion chamber 73 is aspirated through the aperture 83 into the U-tube. As in the continuous flow method, a drug sample is loaded into the tubular loop 70. The multiple connector valve 22 changes to the injection mode and the tubular loop 70 content is injected into the duct 69 from the outlet port of the multiple connector valve 22 to the U-tube 82. The magnetic valve 84 at the outlet of the U-tube 82 is closed, which causes an increase in pressure within the U-tube, thereby forcing a portion of the drug sample through the aperture 83 and into the perfusion chamber 73. After the test of the drug sample is completed, the valve 84 is reopened, stopping the further flow of the drug sample through the aperture 83. The continuous aspiration of the perfusion chamber quickly flushes away the drug sample from the perfusion chamber.

The application time is optional and determined by the period the valve is closed. The use of the U-tube requires a larger experimental perfusion chamber, as shown in FIG. 3. The U-tube is placed on a separate micromanipulator and positioned under visual guidance from the microscope.

The advantage of the U-tube system is that it combines the fast application time needed for studying transmitter regulated channels with the high capacity and low volume requirement of the autosampler.

FIG. 3 shows the flow pattern as it takes place with the U-tube system. This pattern is essentially the same as that in the continuous flow technique, described above. In operation, saline solution is pumped at a steady rate by the peristaltic pump 26 through a duct 67 from the peristaltic pump 26 to the perfusion chamber 73 (this duct does not pass through the multiple connection valve 22). Fluid is also continuously aspirated from the perfusion chamber 73 via duct 68 and the peristaltic pump. The peristaltic pump also continuously pumps normal saline through the U-tube 82. The fluid is pumped through the multiple connection valve 22 and on to the U-tube through duct 69. The general procedure is as follows:

a) A small volume of air is aspirated into the needle 30 by the syringe pump 24, shown in FIG. 1.

b) The needle 30 is moved to a sample vial 28 and aspirates a specified volume of sample.

c) The needle 30 is moved to the injection port 32 and loads the tubular loop 70 with the sample (usually 3 times loop volume; excess volume is rejected through outlet 5).

d) The multiple connector valve 22 changes to the injection mode and the tubular loop 70 content is injected into the duct 69 from the outlet port of multiple connector valve 22 to the U-tube 82.

e) Application occurs by closure of the U-tube outlet by the magnetic valve 84.

f) Upon reopening of magnetic valve 84, the flow of normal saline displaces the sample in the U-tube. The sample solution is flushed from the perfusion chamber 73 by the continuous flow of normal saline pumped from duct 67 and aspirated through duct 68.

g) Before the next application is initiated, the needle 30 is rinsed (perfusion on both sides with reservoir solution) in the rinsing station. The injection port 32 is rinsed by loading reservoir saline through the valve 22 with waste solution discarded through outlet 5.

In order to limit the solution volume and the test compound requirement to an absolute minimum, a stop flow technique according to the present invention was developed.

Figure 4:
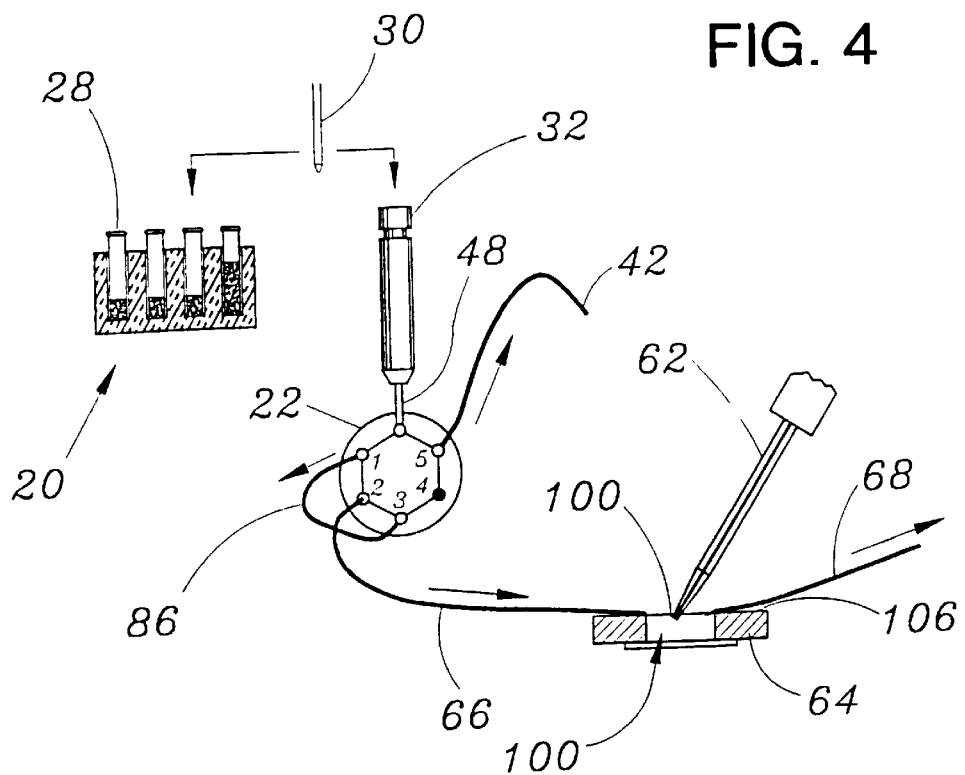
FIG. 4 is a schematic view of a portion of the apparatus as it is modified and utilized in practicing the stop flow technique of the present invention.

Referring to FIG. 4, a somewhat modified arrangement of some of the components is shown for practicing the stop flow technique. The total volume of the dead space including the injection port 32, the multiple connector valve 22, and the tubing is now particularly critical. Consequently, the tubular loop 70 is replaced with a short straight piece of tubing 86 in order to shorten the path of the test solution and thereby reduce the volume of solution required. The volume is reduced to 15 $\mu$l by a special connection of valve inlets and outlets (no loop). In this adaptation the operation of the autosampler is somewhat different from that utilized in HPLC autosamplers. However, the general principle is simple, namely, that the autosampler aspirates a specified volume from a sample vial and loads it directly into the microperfusion chamber 100. The process takes place as follows:

a) A small volume of air is aspirated into the needle 30 by the syringe pump 24, shown in FIG. 1.

b) The peristaltic pump 26, shown in FIG. 1, is automatically activated just before injection, and excess fluid in the microperfusion chamber 100 is aspirated.

c) The needle 30 is moved to a sample vial 28 and aspirates 200 $\mu$l of test solution (control solution+test compound) or saline solution alone.

d) The needle 30 is moved to the injection port. Using the "partial loop filling" option of the sampler, the first 20

μl injected (which possibly contain air-bubbles) is discharged through a waste valve outlet 5 and duct 42.

e) The valve is turned and the remaining solution, 180 μl, is loaded directly to the microperfusion chamber 100 (loading time 15 sec., but in principle optional) with continuous aspiration of excess volume from the chamber 100 by duct 68.

f) After injection, the pump and the liquid flow are stopped for the required period and the necessary electrical measurements are made as an indication of the amount of ion transfer, and the value recorded by the computer.

g) Before the next application is initiated, the needle 30 is rinsed (perfusion on both sides with reservoir solution) in the rinsing station the injection port 32 is rinsed by loading reservoir saline solution through the outlet 5 of the valve 22.

The advantage of the stop flow system is primarily a very low sample volume requirement (maximally 220 μl total). If less perfusion than around 20 times chamber volume is acceptable, the total volume may be decreased accordingly. Experiments performed according to the present invention indicate that more than 90% exchange is obtained by injecting just 100 μl (140 μl total). Such a low volume requirement permits the electrophysiological testing of entire chemical libraries, often based on small amounts of compounds from synthesis and/or isolates from natural products.

Additionally, according to the present invention, several embodiments of microperfusion chamber assemblies have been developed having extremely small microperfusion chambers. The use of these microperfusion chambers provides a system for analyzing extremely small volumes of test samples and supporting liquids, thereby greatly reducing the time required for the testing procedure.

Figure 5:
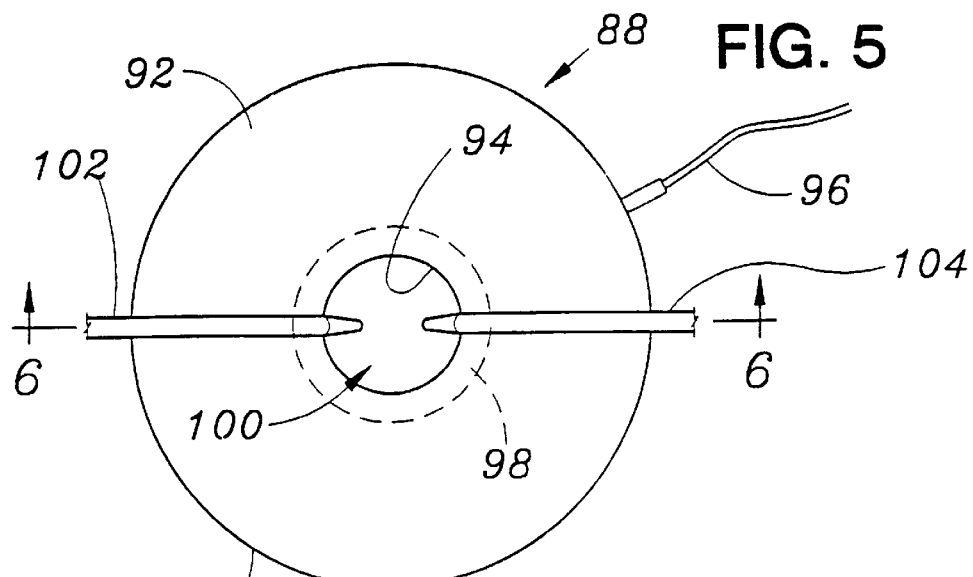
FIG. 5 is a plan view of a microperfusion chamber plate according to one form of the invention.
Figure 6:
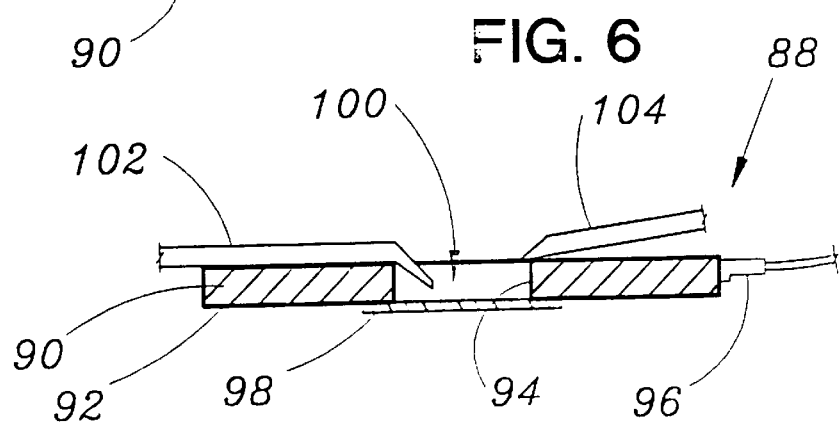
FIG. 6 is a cross-sectional view of the microperfusion chamber plate shown in FIG. 5, taken at the line 6—6 of FIG. 5.

Referring to FIGS. 5 and 6, one embodiment of a very small volume microperfusion chamber assembly 88 is shown. Because of the extremely small size of the chamber, there is insufficient space for two electrodes to be positioned in the microperfusion chamber 100. Consequently, the reference electrode must be an integral part of the chamber structure. In the embodiment shown in FIGS. 5 and 6, the chamber assembly 88 comprises a silver disk 90 coated with a thin layer of silver chloride 92. The silver disk 90 and the silver chloride layer 92 cooperate to serve as a reference electrode. The silver disk 90 has a thickness of 1 mm, and a diameter of 6 mm. A 3 mm aperture 94 is bored into the center of the disk to form the microperfusion chamber 100 cavity. A silver wire 96 is soldered to the silver disk 90. The silver chloride layer 92 is applied to the surface of the silver disk 90 by placing the silver disk 90 in an aqueous solution of sodium chloride and electrolyzing the disk for 2 hours while it is connected as the anode and utilizing a separate silver wire as the cathode. In order to prevent shorting out of the electrode, at least the entire surface of the aperture 94 should be coated with silver chloride. Preferably, the entire silver disk 90 is coated with silver chloride, including the surface of the aperture 94. A glass coverslip 98, 40 mm in diameter and 0.1 mm thick, is adhesively affixed to the bottom of the coated silver disk 90 and over the aperture 94, to form a transparent bottom of the microperfusion chamber 100. The volume of the microperfusion chamber 100 may be in the range of 5–50 μl. More desirable results may be obtained with a microperfusion chamber 100 in the range of 10–15 μl, although the preferred range is 10–12 μl in order to utilize only small samples of the material to be tested and small volumes of supporting liquid, thereby reducing the time required for each test. All solutions enter the chamber through inlet 102 and are aspirated from the chamber through outlet 104.

Cultured cells may be grown in monolayers on small coverslips 74 (thickness 0.1 mm, diameter 2.8 mm) in a standard incubator. Prior to carrying out the experiments, a single coverslip 74 is transferred by thin forceps to the bottom of the microperfusion chamber 100 and superfused with saline. The patch pipette 62, shown in FIG. 1, a standard patch clamp having a final resistance of 2–6 MΩ, is lowered from above as indicated in FIGS. 1, 2, 3, and 4. The patch pipette 62 has a silver-silver chloride electrode 63 mounted therein, and is supported by the patch pipette holder 60, a standard type developed by HEKA Electronics. The diameter of the pipette tip is about 1 μm. Consequently, when the pipette is filled by suction, and back-filling, the solution stays in place due to capillary force. Only a slight suction applied by mouth is necessary for creating a giga-seal between the pipette and the membrane used in the testing. The electrode 63 contained in the patch pipette 62 is electrically connected to the preamplifier (headstage) 61, which is in turn electrically connected to the patch clamp amplifier 78, which is in turn electrically connected to the computer 80. The silver wire 96 is electrically connected to the reference electrode, which comprises the silver disk 90 and the silver chloride layer 92. The reference electrode is connected to the silver wire 96, which is in turn electrically connected to the ground terminal on the preamplifier (headstage) 61. The effect of each sample being tested on ion channel transfer is measured in terms of electrical current flow by the electrode contained in the patch pipette 62 and the reference electrode, and recorded by the computer 80.

Figure 7:
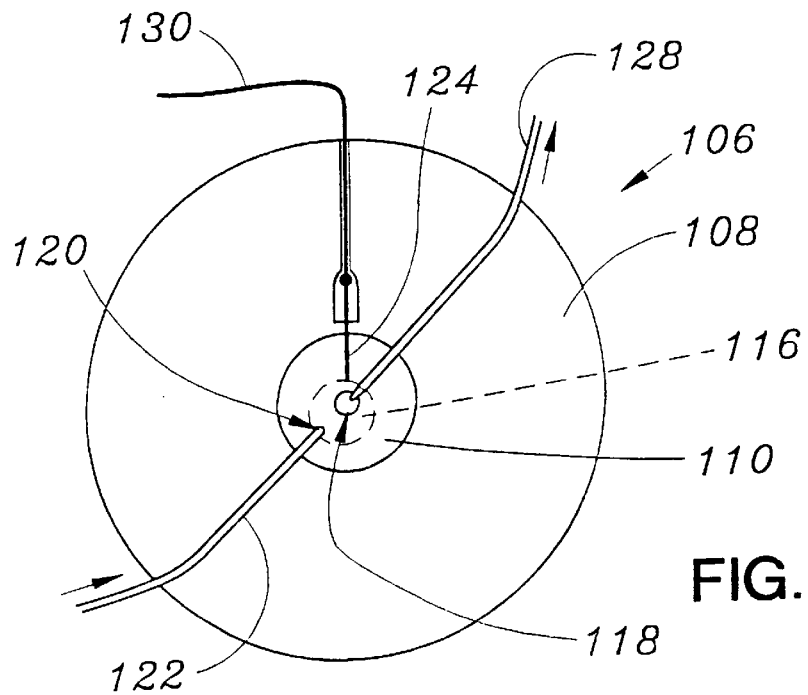
FIG. 7 is a plan view of a microperfusion chamber plate assembly according to another embodiment of the invention.

Referring to FIGS. 7, 8, 9, and 10, a microperfusion chamber assembly 106 in another embodiment is shown. As shown in FIG. 7, the assembly 106 comprises a metal supporting disk 108 designed to fit exactly into the central aperture of the microscope stage 56. Mounted in an aperture provided in the supporting disk 108 is a microperfusion chamber disk 110, shown in detail in FIGS. 8 and 9. The microperfusion chamber disk 110 may be made of any non-electrically conducting materials, among which are plastics including methyl methacrylate, polystyrene, polyvinyl chloride, phenol formaldehyde, or many other materials. An aperture 112 is drilled into the microperfusion chamber disk 110 having a diameter of about 3 mm. A groove 114 is provided in the bottom of the microperfusion chamber disk 110 and a coverslip 116 is cemented to the bottom of the disk 110. The coverslip 116 cooperates with aperture 112 to form a microperfusion chamber 118. The coverslip 116 cooperates with the groove 114 to form a channel 117 for introducing the liquid sample to be tested and the supporting saline solution into the microperfusion chamber 118. An aperture 120 is provided in the upper wall of the disk 110 to serve as a port for the introduction of liquids into the channel 117. A tube 122 connects the aperture with the autosampler multiple connection valve 22 shown in FIG. 1. A small silver/silver chloride pellet electrode 124 is embedded in a groove 126 provided in the upper surface of the disk 110, and serves as a reference electrode. The pellet electrode 124 is formed of a mixture of silver and silver chloride compressed around a silver wire, obtained from IN VIVO METRIC, California. A wire from the electrode 124 is connected directly to the amplifier headstage 78, shown in FIG. 1.

Aspiration of excess fluid from the microperfusion chamber such as 72, 100, or 118 represents a special problem with small chambers, since a large fraction of the total chamber volume is aspirated per second. A very smooth aspiration with a tiny plastic tube 128 (Eppendorf GELoader Tip) can be utilized and is essential to avoid fluctuations in the level of the liquid surface. Unstable liquid surfaces produce a variable background noise and may also confer an increased mechanical stress to the cell or patch, thereby limiting the recording period.

The following examples, given by way of illustration only and not by way of limitation, will provide a clear understanding of the manner in which the invention can be performed.

EXAMPLE 1

CONTINUOUS FLOW TECHNIQUE: The calcium current of a chick dorsal root ganglion cell was determined in whole-cell recording using the continuous-flow technique utilizing an apparatus as disclosed above and diagramed in FIGS. 7–10, comprising an autosampler, syringe pump, peristaltic pump, and microperfusion chamber having a volume of 12 μl.

The $Ca^{2+}$ currents were isolated from other currents by use of the following pipette and bath solutions:

Pipette: CsCl (100 mM), CsF (20 mM), EGTA (10 mM), $MgCl_2$ (4 mM), HEPES (10 mM).

Bath: NaCl (140 mM), KCl (4 mM), $CaCl_2$ (2 mM), $MgCl_2$ (1 mM), HEPES (10 mM), TTX (0.3 μM). The high Calcium concentration blocks $K^+$ currents, whereas TTX (tetrodotoxin) blocks $Na^+$ currents.

Figure 11:
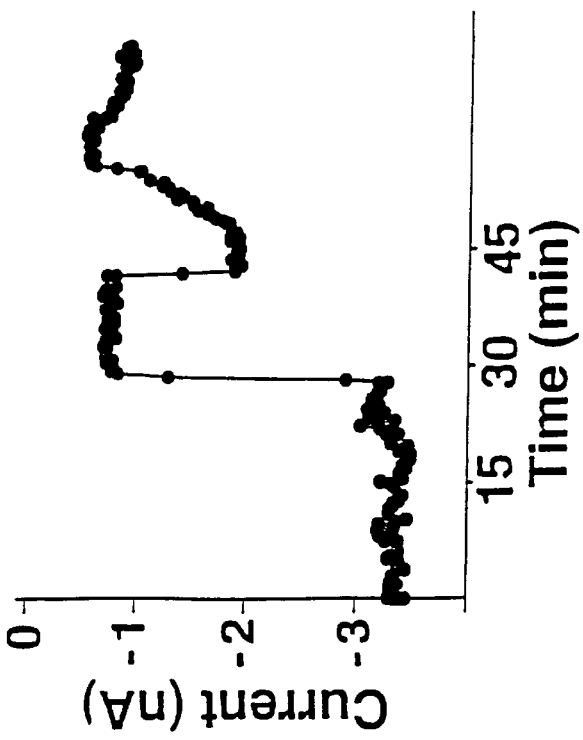
FIG. 11 is a graph displaying the effect of reference compounds on voltage dependent calcium channels; and, FIG. 12 is a graph displaying the effect of test compounds on calcium-activated potassium channels.

The effects of five known standards, phenytoin, amiloride, ω-conotoxin MVIIA, Bay-k 8644, and nifedipine on voltage dependent calcium channels were tested in sequence and are reported in FIG. 11. The graphical presentation indicates successive recordings of the maximum current induced by 5 msec depolarizing voltage steps to 0 mV from the −70 mV resting potential. The compounds were perfused in 500 μl aliquots. Neither phenytoin nor amiloride, injected at the 0 and 15 minute timepoints respectively, affected the current, indicating no effect on calcium ion channels. At the 30 minute timepoint, a 500 μl aliquot of ω-conotoxin MVIIA was injected. The ω-conotoxin MVIIA has a high affinity for N-type calcium channels as demonstrated by the current modulation recorded on the graph. The graph also demonstrates that the ω-conotoxin MVIIA binding was irreversible because no washout is evident from the graph. Bay-k 8644 and nifedipine were injected at 45 minutes and 1 hour respectively. Bay-k 8644 stimulates L-type calcium channels reversibly, as is evident from the washout over time. Nifedipine blocks the L-type calcium channel.

The invention is thus demonstrated to be useful in determining the response of patch-clamp isolated membrane ion channels to perfusion with compounds having well-known physiological activity. The results indicate that five compounds were tested in little more than one hour using a single membrane preparation, and exhibiting a useful range of physiological response. In practice, screening of unknown compounds including application periods as well as washout periods between applications are shorter and therefore ten to twenty compounds can be screened in the course of an hour. (See especially Example 2.)

EXAMPLE 2

STOP-FLOW TECHNIQUE: The potassium current of a cultured human coronary smooth muscle cell was determined in an excised inside out patch by the stop-flow technique utilizing an apparatus as disclosed above and diagramed in FIGS. 7–10, comprising an autosampler, syringe pump, and microperfusion chamber having a volume of 12 μl.

The composition of the pipette and bath solutions was:

Pipette: KCl (140 mM), $CaCl_2$ (1 mM), $MgCl_2$ (1 mM), EGTA (1.3 mM), HEPES (10 mM).

Bath: KCl (140 mM), $CaCl_2$ (1 mM), $MgCl_2$ (1 mM), EGTA from 1.07 mM to 2.0 mM. The free $Ca^{2+}$ concentration is determined by the concentration of EGTA. All test compounds were dissolved in bath solution with 0.3 μM free $Ca^{2+}$.

Figure 12:
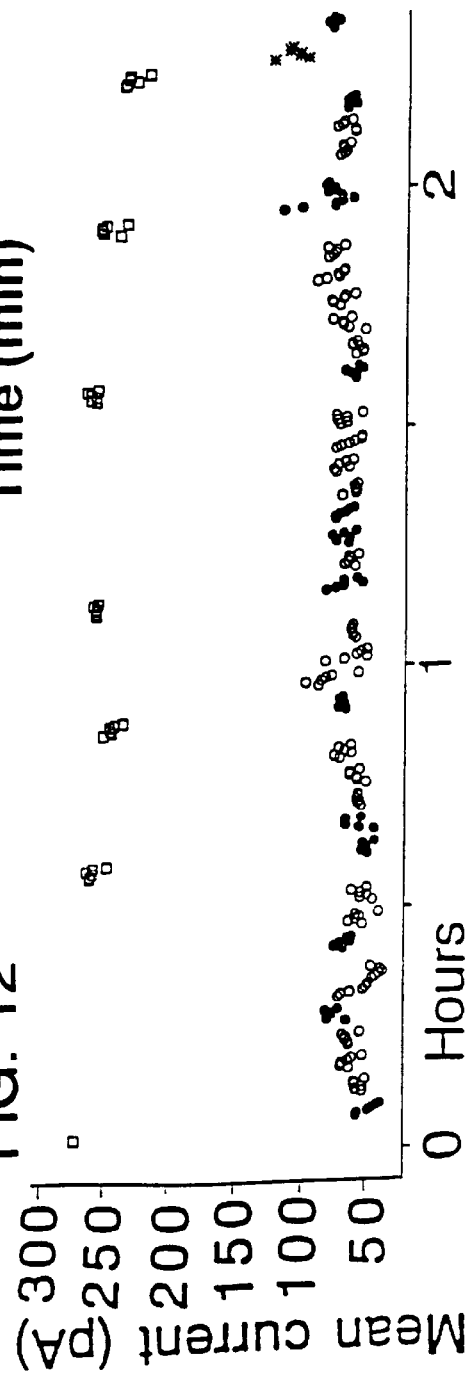

The effects of 25 unknown compounds on calcium activated potassium channels were tested and reported in FIG. 12. In the experimental protocol, successive unknown compounds (open circles) were perfused (300 μl) with intermittent washout with saline solution (filled circles). Each application lasted 2 minutes and is reported as six (6) data points. Multiple channels were present in the patch and their activity was adjusted to a low level (20% of full activity) by a bath solution having a low free calcium ion concentration (0.3 μM). This level was chosen to be able to detect both possible activating and blocking effects of the unknown test compounds. At various intervals full activation was induced by perfusion with saline solution containing 1 μM free calcium ion concentration (open squares). Perfusion with saline solution containing 0.5 μM free calcium ion was tested at the end (asterisk *). In this particular test of 25 unknowns at a concentration of 1 μM, no compound induced a change from the basal calcium activated potassium current, but the potassium channels of the membrane preparation exhibited characteristic high potassium current when exposed to the high (1.0 μM) calcium concentration saline solution.

The invention is thus demonstrated to provide a mechanism whereby small volumes of test compounds can be analyzed in rapid succession. The test is remarkable because over twenty-five (25) unknown test compounds were screened in the course of a two hour time period. The test was validated by intermittent full activation of K-channels induced by perfusion with saline solution having a higher free calcium ion concentration. This high calcium induced potassium current demonstrates the scope of current response available from the membrane preparation, evidencing the sensitivity necessary to detect an active compound.

The present invention provides a novel way of utilizing an HPLC autosampler in carrying out patch clamp techniques. This enables a large number of tests to be carried out in a relatively short time period. The invention also comprises the use of novel microperfusion chamber assemblies containing very small microperfusion chambers, thereby enabling very small amounts of test sample solutions and supporting solutions to be utilized, and additionally reducing the amount of time required for each test. The invention also includes several novel procedures for carrying out the patch clamp technique providing even further benefits. The invention further includes novel microperfusion chamber structures utilizing very small chambers and having integral electrodes.

In the following claims, the term "membrane" is employed to designate whole cells or partial cell membranes.

Although preferred embodiments of the invention have been illustrated in the accompanying drawings and described in the foregoing Specification, it is to be understood that the invention is not limited to the exact embodiments disclosed or to the exact details of operation or exact methods or procedures shown and described, since the invention is capable of numerous modifications, rearrangements, and substitutions of parts and elements and other equivalents, without departing from the spirit or scope of the invention, as will readily be apparent to one skilled in the art, wherefore the present invention is to be understood as limited only by the full scope which can be legally accorded the appended claims.

We claim:

1. Apparatus for determining the effect of test samples of compounds on ion-transfer channels of a membrane, comprising:

an autosampler having a plurality of containers adapted to contain test samples in solution, and having means for automatically withdrawing said test samples from each of said containers and discharging them into a receptacle, a container adapted to contain a supporting liquid, a perfusion chamber adapted to receive a test sample in solution, a supporting liquid, and said membrane, said perfusion chamber being open to the atmosphere at the top, and comprising a reference electrode adapted to contact electrically a solution contained in said chamber, means for transporting said test samples in solution from the receptacle of said autosampler and said supporting liquid from its container into said perfusion chamber, and means for removing said test sample and said supporting liquid from said perfusion chamber, a patch pipette having an electrode therein, movably positioned over said perfusion chamber and adapted to provide a high electrical resistance seal with the surface of a patch of said membrane positioned within said chamber, and means electrically connected to said patch pipette electrode and said reference electrode for measuring the current passing through said electrodes before and after the introduction of said test sample into said perfusion chamber.

2. Apparatus according to claim 1, wherein the means for transporting test samples and supporting liquid to said perfusion chamber includes a U-tube mounted over said perfusion chamber and having an aperture therein for releasing a test sample and its supporting liquid into said perfusion chamber.

3. Apparatus for determining the effect of test samples of compounds on ion-transfer channels of a membrane, comprising:

an autosampler having a plurality of containers adapted to contain test samples in solution, and having means for automatically withdrawing said test samples from each of said containers and discharging them into a receptacle, a container adapted to contain a supporting liquid, a microperfusion chamber adapted to receive a test sample in solution, a supporting liquid, and said membrane, said microperfusion chamber being open to the atmosphere at the top, the volume of said microperfusion chamber being about 5 microliters to about 50 microliters, said microperfusion chamber comprising a reference electrode adapted to contact electrically a solution contained in said chamber, means for transporting a test sample in solution from the receptacle of said autosampler and said supporting liquid from its container into said microperfusion chamber and means for removing said test sample and said supporting liquid from said microperfusion chamber, a patch pipette having an electrode therein, movably positioned over said microperfusion chamber and adapted to provide a high electrical resistance seal with the surface of a patch of said membrane positioned within said chamber, and means electrically connected to said patch pipette electrode and said reference electrode for measuring the current passing through said electrodes before and after the introduction of a test sample into said microperfusion chamber.

4. Apparatus according to claim 3, wherein the volume of said microperfusion chamber is in the range of about 10 microliters to about 15 microliters.

5. Apparatus according to claim 3, wherein the volume of said microperfusion chamber is in the range of about 10 microliters to about 12 microliters.

6. Apparatus according to claim 3, having means for aspirating waste liquid from said microperfusion chamber.

7. Apparatus according to claim 3, wherein said means of said autosampler for automatically withdrawing said test samples from said containers and discharging them into a receptacle comprises a syringe pump and a needle connected thereto.

8. Apparatus according to claim 3, wherein a tubular coil is positioned in series with said means for transporting said test sample for quantitatively determining the volume of the sample introduced into said microperfusion chamber.

9. A method for determining the effect of test samples of compounds on ion-transfer channels of a membrane contained in a perfusion chamber, wherein a patch pipette having an electrode therein has its tip engaged in a giga-ohm seal with the surface of said membrane, and wherein a reference electrode is provided in said chamber adapted to contact a solution contained in said chamber, said chamber being open to the atmosphere at the top, comprising:

continuously or periodically introducing a supporting liquid containing ions, the transfer characteristics of which are to be determined as a baseline reference, into said chamber, periodically loading one of said test samples dissolved in the same supporting liquid into said chamber utilizing an autosampler having a plurality of containers holding test samples in solution, and measuring the electrical current flowing in an electrical measuring means circuit connected between said pipette electrode and said reference electrode both before and after introduction of said test sample into said perfusion chamber, and repeating the procedure.

10. A method of claim 9, wherein said supporting liquid is continuously introduced into said perfusion chamber and the excess aspirated, and wherein said autosampler is programmed periodically to introduce a test sample into the flowing stream of said supporting liquid to flow therewith into said perfusion chamber.

11. A method of claim 10, wherein said perfusion chamber is a microperfusion chamber having a volume of 5 microliters to about 50 microliters.

12. A method of claim 11, wherein the volume of said microperfusion chamber is about 10 microliters to about 15 microliters.

13. A method of claim 11, wherein the volume of said microperfusion chamber is about 10 microliters to about 12 microliters.

14. A method of claim 13, wherein an external electrical current is imposed on said electrodes to establish a reference current at a desired value.

15. A method of claim 9, wherein said supporting liquid is periodically introduced into said perfusion chamber and the excess aspirated, and wherein said autosampler is programmed periodically to cause a test sample to flow into said perfusion chamber.

16. A method of claim 15, wherein some of said containers in said autosampler contain said supporting liquid and wherein said autosampler is programmed periodically to introduce said supporting liquid and said test sample sequentially into said perfusion chamber.

17. A method according to claim 9 wherein only small volumes of both test samples and supporting liquid are employed, wherein said perfusion chamber is a microperfusion chamber having a volume of about 5 to about 50 microliters, wherein some of the containers in said autosampler contain said supporting liquid, and wherein said autosampler first aspirates a volume of supporting liquid from one of said containers and causes the supporting liquid to enter said microperfusion chamber, and wherein said autosampler subsequently aspirates a test sample from one of said containers and causes the test sample to enter said microperfusion chamber and to replace said supporting liquid in said chamber, and wherein an electrical measurement is made both when said supporting liquid and when said test sample are present in said microperfusion chamber.

18. A method of claim 17, wherein the volume of said microperfusion chamber is about 10 microliters to about 15 microliters.

19. A method of claim 17, wherein the volume of said microperfusion chamber is about 10 microliters to about 12 microliters.

20. A method of claim 19, wherein an external electrical current is imposed on said electrodes to establish a reference current at a desired value.

* * * * *

UNITED STATES PATENT AND TRADEMARK OFFICE
CERTIFICATE OF CORRECTION

PATENT : 6,063,260
DATED : May 16, 2000
INVENTOR(S) : S-P Olesen and P. Christophersen It is certified that error appears in the above-identified patent and that said Letters Patent is hereby corrected as shown below:

Column 4, line 27: "contained iii" should read:
-- contained in --. Page 7, line 10

Column 13, line 15: Insert a -- . -- (period) after
the word "station". Page 3, line 19

Signed and Sealed this

Twentieth Day of March, 2001

Attest:

NICHOLAS P. GODICI

*Attesting Officer*     *Acting Director of the United States Patent and Trademark Office*